United States Patent [19]

Theissen

[11] Patent Number: 4,667,052

[45] Date of Patent: May 19, 1987

[54] 2-NITRO-5-(SUBSTITUTED PHENOXY) BENZOATE ESTERS OF HYDROXYALKANOIC ACIDS AND DERIVATIVES THEREOF AS HERBICIDES

[75] Inventor: Robert J. Theissen, Bridgewater, N.J.

[73] Assignee: Rhone-Poulenc Inc., Monmouth Junction, N.J.

[21] Appl. No.: 484,702

[22] Filed: Apr. 13, 1983

Related U.S. Application Data

[63] Continuation of Ser. No. 274,105, Jun. 16, 1981, which is a continuation-in-part of Ser. No. 117,753, Feb. 1, 1980.

[51] Int. Cl.[4] ............................................. C07C 79/46
[52] U.S. Cl. ........................................ 560/21; 71/107; 71/108; 71/111
[58] Field of Search ..................... 71/107, 108, 111; 560/21

[56] References Cited

U.S. PATENT DOCUMENTS

| | | | |
|---|---|---|---|
| 3,784,635 | 1/1974 | Theissen | 560/21 |
| 4,031,131 | 6/1977 | Johnson | 560/21 |
| 4,106,925 | 8/1978 | Rohr | 560/21 |
| 4,259,510 | 3/1981 | Johnson | 560/21 |
| 4,400,530 | 8/1983 | Grove | 560/21 |

FOREIGN PATENT DOCUMENTS

| | | |
|---|---|---|
| 0020052 | 12/1980 | European Pat. Off. . |
| 0021692 | 1/1981 | European Pat. Off. . |
| 0062637 | 6/1974 | Japan . |
| 2058055 | 4/1981 | United Kingdom . |

*Primary Examiner*—Paul J. Killos
*Attorney, Agent, or Firm*—Morgan & Finnegan

[57] ABSTRACT

There is provided a new class of derivatives of 2-nitro-5-(substituted-phenoxy) benzoate esters of hydroxyalkanoic acids that have pre- and post-emergence herbicidal activity.

21 Claims, No Drawings

2-NITRO-5-(SUBSTITUTED PHENOXY) BENZOATE ESTERS OF HYDROXYALKANOIC ACIDS AND DERIVATIVES THEREOF AS HERBICIDES

CROSS-REFERENCE TO RELATED APPLICATIONS

This is a continuation of application Ser. No. 274,105 filed June 16, 1981, which in turn is a continuation-in-part of application Ser. No. 117,753 filed Feb. 1, 1980.

Applicant Theissen herein has been granted a series of patents relating to 2-nitro-5-(substituted-phenoxy) benzoic acid derivatives including the salt, alkyl and cycloalkyl esters, alkylthio esters, phenyl ester, alkyl and dialkyl amido and benzoyl chloride forms. Illustrative of those patents are U.S. Pat. Nos. 3,652,645; 3,784,635; 3,873,302; 3,983,168 and 3,907,866.

FIELD OF THE INVENTION

This invention is concerned with certain herbicidal 2-nitro-5-(substituted phenoxy) benzoate esters of hydroxyalkanoic acids and derivatives thereof.

BRIEF SUMMARY OF THE INVENTION

This invention provides certain herbicidal compounds within the class of 2-nitro-5-(substituted-phenoxy) benzoate esters of hydroxy alkanoic acids and derivatives thereof wherein there are, e.g., up to six carbon atoms in the alkanoic acid moiety. Preferred members of this class are the alpha-hydroxy alkanoic acids and derivatives which fall within the general formula:

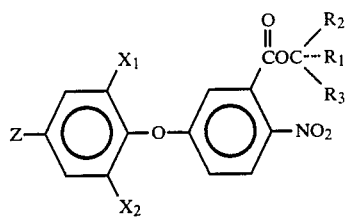

wherein $X_1$ is halogen, $X_2$ is selected from halogen and hydrogen, and

Z is a halogen-containing group such as a polyhalo$_{1-9}$ alkyl$_{1-4}$ group such as $CF_3$, $CHF_2$, $C_4F_9$, $CF_2CH_2CH_3$ and $CH_2Cl$.

$R_1$ is selected from COOH, COOM where M is a cation selected from alkali metals, alkaline earth metals, ammonium, alkyl$_{1-5}$ and dialkyl$_{2-6}$ ammonium; and

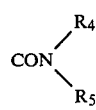

where $R_4$ and $R_5$ are selected from hydrogen and alkyl$_{1-5}$.

$R_2$ and $R_3$ may be the same or different and each is selected from hydrogen; alkyl$_{1-5}$; and QCOOR$_6$ where Q is alkyl$_{0-3}$, $R_6$ is alkyl$_{1-5}$, hydrogen, a cation selected from alkali metals, alkaline earth metals, ammonium and alkyl$_{1-5}$ and dialkyl$_{1-5}$ ammonium or

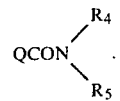

$R_1$ may additionally be COOR$_7$ where $R_7$ is alkyl$_{1-5}$ when (i) $R_2$ and $R_3$ are both alkyl or (ii) when at least one of $R_2$ and $R_3$ is selected from QCOOR$_6$ and

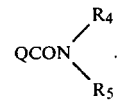

The term "alkyl" means straight or branched carbon chains where the carbon length is in the range set forth in the adjacent subscript.

Alkanoic acids and derivatives of the present invention also include those other than the alpha-hydroxy type described hereinabove. Such compounds would include unsaturated alkanoic acids and derivatives, e.g., where Q is an alkenyl of two to six carbons. Other alkanoic acids and derivatives of the present invention include compounds of Formula I wherein $R_1$ is a carboxyalkyl group or derivative thereof such as where $R_1$ is QCOOR$_6$, Q being an alkyl of one to three carbons.

DETAILED DESCRIPTION OF THE INVENTION

The specific 2-nitro-5-(substituted-phenoxy) benzoate ester compounds are described below. One method for preparing these compounds is the use of the Ullmann ether synthesis reaction between the alkali metal (e.g., Na, K) salt of a suitable substituted phenol, e.g., m-hydroxy benzoic acid or m-cresol with an active halogen-substituted aromatic, e.g., 3,4-dichlorobenzotrifluoride. The intermediate obtained may be nitrated and subsequently derivatized. Where m-cresol is used as a starting material, the product obtained can be oxidized and subsequently nitrated before derivatization. The derivatization steps may be carried out by known techniques. One such technique is the reaction of the appropriate halo-alkanoic acid or derivative with the salt of the particular 2-nitro-5(substituted phenoxy) benzoic acid. Another technique is the reaction of the desired hydroxy alkanoic acid or derivative with the particular 2-nitro-5(substituted phenoxy) benzoyl halide.

Compound 1

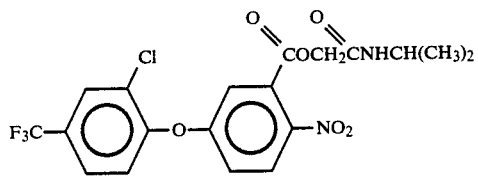

Preparation of (2-propylaminocarbonyl) methyl 5-[2-chloro-4-(trifluoromethyl)phenoxy]-2-nitrobenzoate.

To a solution of 5-[2-chloro-4(trifluoromethyl) phenoxy]-2-nitrobenzoic acid (3.62 g., 0.01 mole) in methanol (25 ml) was added potassium t-butoxide (1.12 g., 0.01 mole). The solution was stirred for 0.5 hours as a solid formed. The solvent was stripped on a rotary evaporator. The resulting solid was then dissolved in dimethylacetamide (25 ml) and N-isopropyl alphachloro acetamide (1.36 g., 0.01 mole) was added. The stirred solution was heated to about 80° C. for 15 hours, cooled and poured into water (75 ml). A yellow solid formed and was filtered, washed and dried to give 4.17 g., m.p. 100°-102° C.

I.R. (nujol): C=O 1733 and 1665 cm$^{-1}$.

NMR (CDCl$_3$): Doublet 1.18 ppm (J=8.0 HZ, 6H); Multiplet 4.20 ppm (1H); Singlet 4.80 ppm (2H); Broad doublet 6.30 ppm (1H); Complex multiplet 7.1–8.0 ppm (6H); Doublet 8.20 ppm (J=8.2 HZ, 1H).

Compound 2

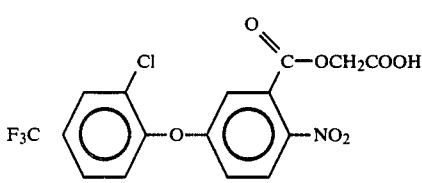

Preparation of carboxymethyl 5-[2-chloro-4-(trifluoromethyl)phenoxy]-2-nitrobenzoate.

A solution of (t-butoxycarbonylmethyl) 5-[2-chloro-4-(trifluoromethylphenoxy)-2-nitrobenzoate (4.24 g, 0.009 mole) in trifluoroacetic acid (10 ml) was heated on a steam bath at 100° C. for 0.5 hour to effect the hydrolysis and distill out the trifluoroacetic acid. The residue was dissolved in methylene chloride, washed with water and the dried solution stripped free of solvent. Any oily yellow solid was obtained in 97% yield.

IR (CHCl$_3$): C=O 1740 cm$^{-1}$ broad.

NMR (CDCl$_3$): Singlet 5.0 ppm (2H); Complex multiplet 7.1–8.4 ppm (6H); Broad singlet 10.8 ppm (1H).

Compound 3

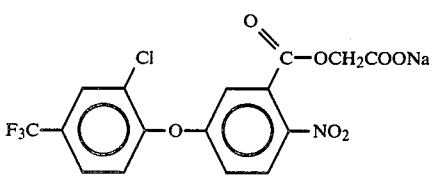

Preparation of carboxymethyl 5-[2-chloro-4-(trifluoromethyl)phenoxy]-2-nitrobenzoate sodium salt.

A sodium hydride suspension (146 mg of 59% in oil, 0.0035 mole) was washed twice with hexane and then diluted with benzene (10 ml). To this was added carboxymethyl 5-[2-chloro-4-(trifluoromethyl)phenoxy]-2-nitrobenzoate (1.38 g, 0.0033 mole) in benzene (10 ml). The solution was stirred at 0° C. and the solvent was then removed to give a viscous yellow oil.

IR (CHCL$_3$): C=O 1730 and 1620 cm$^{-1}$.

NMR (CDCl$_3$): Singlet 4.70 ppm (2H); Complex multiplet 6.7–8.2 ppm (6H).

Compound 4

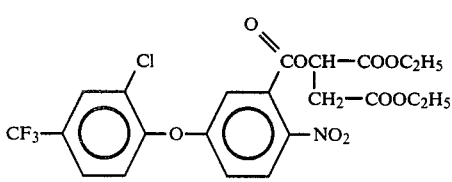

Preparation of 1,2-bis-(ethoxycarbonyl)ethyl 5-[2-chloro-4-(trifluoromethyl)phenoxy]-2-nitrobenzoate.

To a stirred solution of 5-[2-chloro-4-(trifluoromethyl)phenoxy]-2-nitrobenzoyl chloride (3.8 g, 0.01 mole) in acetone (10 ml) was successively added diethyl DL malate (1.9 g, 0.01 mole) in acetone (10 ml) and triethylamine (1.01 g, 0.01 mole) in acetone (5 ml). A white precipitate quickly formed. The reaction was heated to reflux for 24 hours. Upon cooling, the reaction was poured in water (75 ml) and extracted twice with methylene chloride (25 ml @). The combined organic extracts were successively washed with 5% sodium hydroxide and brine solutions. The dried solution was stripped of solvent to give 3.56 g of an amber oil.

IR (neat): C=O 1740 cm$^{-1}$ (broad).

NMR (CDCl$_3$): Triplet 1.38 ppm (6H, J=7.0 HZ); Doublet 3.05 ppm (2H, J=6.0 HZ); 2 overlapping sets of quartets 4.0–4.5 ppm (4H); Triplet 5.82 ppm (1H, J=6.0 HZ); Complex multiplet 7.0–8.0 ppm (5H); Doublet 8.20 ppm (1H, J=9.0 HZ).

In addition to compounds 1–4, the following compounds listed in Table I were prepared in accordance with the following formula:

TABLE I

| COMPOUND NO. | R$_1$ | R$_2$ | R$_3$ | |
|---|---|---|---|---|
| 5 | COOC$_2$H$_5$ | H | COOC$_2$H$_5$ | bis-(ethoxycarbonyl) methyl 5-[2-chloro-4-(trifluoromethyl)phenoxy]-2-nitrobenzoate |
| 6 | CON(C$_2$H$_5$)$_2$ | H | CH$_3$ | (diethylaminocarbonyl)-1-ethyl 5-[2-chloro-4-(trifluoromethyl)phenoxy]-2-nitrobenzoate |
| 7 | CH$_2$COOC$_2$H$_5$ | H | CH$_3$ | 1-(ethoxycarbonyl)-2-propyl 5-[2-chloro-4-(trifluoromethyl)phenoxy]-2-nitrobenzoate |
| 8 | COOCH$_3$ | CH$_3$ | CH$_3$ | 2-(methoxycarbonyl)-2-propyl 5-[2-chloro-4-trifluoromethyl)phenoxy]-2-nitrobenzoate |
| 9 | CONH$_2$ | H | H | (aminocarbonyl)methyl 5-[2-chloro-4-(trifluoromethyl)phenoxy-2-nitrobenzoate |
| 10 | COOH | H | CH$_3$ | (1-carboxyethyl) 5-[2-chloro-4-(trifluoromethyl)phenoxy]-2-nitrobenzoate |

Other illustrative alpha-hydroxy alkanoic acids and derivatives of the present invention are listed in Table II in accordance with the formula given for Table I.

TABLE II

| R₁ | R₂ | R₃ | |
|---|---|---|---|
| COOH | CH₂COOH | CH₂COOH | (1,2,3-tricarboxy)-2-propyl 5-[2-chloro-4-(trifluoromethyl) phenoxy]-2-nitrobenzoate |
| CONHCH₃ | H | H | (methylaminocarbonyl) methyl 5-[2-chloro-4-(trifluoromethyl) phenoxy]-2-nitrobenzoate |
| CON(C₂H₅)₂ | H | H | (diethylaminocarbonyl) methyl 5-[2-chloro-4-(trifluoromethyl) phenoxy]-2-nitrobenzoate |
| COOC₄H₉ | CH₃ | CH₃ | 2-(n-butoxycarbonyl)-2-propyl 5-[2-chloro-4-(trifluoromethyl) phenoxy]-2-nitrobenzoate |
| CQONH₂(CH₃)₂ | CH₃ | CH₃ | 2-carboxy-2-propyl 5-[2-chloro-4-(trifluoromethyl) phenoxy]-2-nitrobenzoate dimethylammonium salt |
| COOH | CH₃ | CH₃ | 2-carboxy-2-propyl 5-[2-chloro-4-(trifluoromethyl) phenoxy]-2-nitrobenzoate |
| CON(C₃H₇)₂ | H | C₂H₅ | (1-dipropylaminocarbonyl)propyl 5-[2-chloro-4-(trifluoromethyl) phenoxy]-2-nitrobenzoate |
| COOH | H | C₃H₇ | (1-carboxy) n-butyl 5-[2-chloro-4-(trifluoromethyl) phenoxy]-2-nitrobenzoate |
| CONHC₂H₅ | CH₃ | CH₃ | 2-(ethylaminocarbonyl)-2-propyl 5-[2-chloro-4-(trifluoromethyl) phenoxy]-2-nitrobenzoate |
| COOCH₃ | C₄H₉ | C₄H₉ | 5-(methoxycarbonyl)-5-nonyl 5-[2-chloro-4-(trifluoromethyl) phenoxy]-2-nitrobenzoate |
| COOCH₃ | H | (CH₂)₃COOCH₃ | (1,4-bis-methoxycarbonyl) n-butyl 5-[2-chloro-4-(tri-fluoromethyl) phenoxy]-2-nitrobenzoate |
| COONa | H | CH₂COONa | (1,2-bis-carboxy) ethyl 5-[2-chloro-4-(trifluoromethyl) phenoxy]-2-nitrobenzoate disodium salt |
| COOC₂H₅ | C₂H₅ | CH₃ | 2-(ethoxycarbonyl)-2-butyl 5-[2-chloro-4-(trifluoromethyl) phenoxy]-2-nitrobenzoate |
| CONH₂ | H | CONH₂ | bis-(aminocarbonyl) methyl 5-[2-chloro-4-(trifluoromethyl) phenoxy]-2-nitrobenzoate |
| COOH | H | COOH | (1,2-bis-carboxy) methyl 5-[2-chloro-4-(trifluoromethyl) phenoxy]-2-nitrobenzoate |
| COOH | COOH | CH₃ | (1,1-bis-carboxy) ethyl 5-[2-chloro-4-(trifluoromethyl) phenoxy]-2-nitrobenzoate |

Primary Herbicide Screening

The compounds of this invention can be applied in various ways to achieve herbicidal action. They can be applied per se, as solids or in vaporized form, but are preferably applied as the toxic components in pesticidal compositions of the compound and a carrier. These compositions may be applied directly to the soil and often incorporated therewith. The compositions can be applied as granulars or dusts; as liquid sprays, or as gas-propelled sprays and can contain, in addition to a carrier, additives such as emulsifying agents, binding agents, gases compressed to the liquid state, odorants, stabilizers, and the like. A wide variety of liquid and solid carriers can be used. Non-limiting examples of solid carriers include talc, bentonite, diatomaceous earth, pyrophyllite, fullers earth, gypsum, flours derived from cotton seeds and nut shells, and various natural and synthetic clays having a pH not exceeding about 9.5. Non-limiting examples of liquid carriers include water, organic solvents such as alcohols, ketones, light oils, and medium oils and vegtable oils such as cottonseed oil.

In practice, herbicidal application is measured in terms of pounds of herbicide applied per acre. The compounds of this invention are effective herbicides when applied in herbicidal amounts, i.e., at rates between about 0.03 pound and about 10 pounds per acre.

HERBICIDAL EFFECTIVENESS

Method of Propagating Test Species

Crop and weed species are planted in 8"×10" disposable fiber flats containing potting soil to provide each flat with a 4" row of all test species. Crop species consist of field corn (CN), crabgrass (CG), cotton (CT), and soybeans (SB). The weed species consist of foxtail millet (FM), green foxtail (GF), velvetleaf (VL), cocklebur (CB), wild mustard (WM) and pigweed (PW).

Cotton, corn, soybean, and cocklebur plantings consist of 4 to 5 seeds per row depending upon species. The smaller seeded species (velvetleaf, wild mustard, pigweed, foxtail millet and green foxtail) are planted in an uncounted but sufficient number to provide a solid row of seedlings.

Plantings for the pre- and post-emergence portions of the test are identical as to seeding. The initial watering until emergence is done from the top. The post-emergence phase is propagated in advance so as to provide plants of the proper stage of development at the time of treatment. Plantings for the pre-emergence phase are made not more than one day in advance of treatment.

The desired stage of development for treatment of the post-emergence broadleaf species (CT, SB, CB, VL, WM, PW) is the one true leaf or first trifoliate leaf stage. The desired stage for corn would be a height of 3–4", while a 2" height would be adequate for the grasses.

Method of Treatment

Spray applications are made with a handgun sprayer (aspirator type) simultaneously to one flat of established plants for the post-emergence phase and one newly seeded flat for the pre-emergence phase. The 10 lb./acre treatment rate consists of the uniform application of 116 milligrams of test compound to the combined area of the two flats (160 sq. inches). Application is made in a solvent mixture consisting of 40 ml acetone and 40 ml water and a surfactant concentration of 0.1%.

Following spray application, flats are returned to the greenhouse where watering of the post-emergence phase is done only by subirrigation. The pre-emergence phase is top watered by sprinkling until after test species have emerged. Subsequent watering is by subirrigation.

Two weeks after treatment, the pre- and post-emergence injury and control is rated on a 0–100% injury and control scale. Special physiological effects are rated as to the intensity also at this time.

The herbicidal test data reported from Compounds 1–3 was obtained at application rates of 2 lbs. down to ¼ lb./acre. The following lists metric equivalents for each rate expressed in terms of lbs./acre.

| Application Rate | |
|---|---|
| US - lb./acre | Metric - kg/ha |
| 10.0 | 11.2 |
| 4.0 | 4.48 |
| 2.0 | 2.24 |
| 1.0 | 1.12 |
| 0.5 | 0.56 |
| 0.25 | 0.28 |

Test results are set forth in Table III.(pre-emergence) and Table IV (post-emergence).

TABLE III

| Compound No. | Dosage Lbs./Acre | Pre-emergence | | | | | | | | | |
|---|---|---|---|---|---|---|---|---|---|---|---|
| | | CG | FM | GF | VL | CB | WM | PW | CT | CN | SB |
| 1 | 2 | — | 90 | 90 | 20 | 60 | 100 | 100 | 10 | 0 | — |
| | 1 | — | 90 | 90 | 10 | 30 | 90 | 100 | 20 | 10 | 0 |
| | ½ | — | 60 | 30 | 10 | 0 | 90 | 60 | 0 | 0 | 0 |
| 2 | 2 | — | 100 | 30 | 40 | 0 | 100 | 100 | 10 | 10 | 10 |
| | 1 | — | 90 | 20 | 20 | 0 | 100 | 70 | 0 | 0 | 0 |
| | ½ | — | 80 | 20 | 20 | 0 | 90 | 50 | 0 | 0 | 0 |
| | ¼ | — | 40 | 0 | 10 | 0 | 30 | 20 | 0 | 0 | 0 |
| 3 | 2 | — | 90 | 70 | 80 | 0 | 100 | 100 | 20 | 10 | 0 |
| | 1 | — | 70 | 10 | 50 | 0 | 100 | 100 | 10 | 0 | 0 |
| | ½ | — | 20 | 0 | 10 | 0 | 90 | 100 | 0 | 0 | 0 |
| | ¼ | — | 10 | 0 | 0 | 0 | 70 | 100 | 0 | 0 | 0 |
| 4 | 2 | — | 40 | 10 | 60 | 10 | 90 | 100 | 10 | 0 | 0 |
| | ½ | — | 30 | 20 | 10 | 0 | 90 | 90 | 0 | 0 | 0 |
| | ¼ | — | 10 | 20 | 10 | 0 | 80 | 100 | 10 | 10 | 0 |
| 5 | 2 | — | 100 | 90 | 30 | 0 | 100 | 100 | 20 | 0 | 0 |
| | 1 | — | 90 | 70 | 20 | 0 | 90 | 100 | 10 | 10 | 0 |
| | ½ | — | 90 | 40 | 20 | 0 | 70 | 100 | 10 | 0 | 0 |
| | ¼ | — | 70 | 10 | 10 | 0 | 40 | 90 | 0 | 0 | 10 |
| 6 | 2 | — | 80 | 70 | 70 | 0 | 90 | 100 | 10 | 0 | 0 |
| | 1 | — | 90 | 20 | 50 | 0 | 70 | 100 | 0 | 0 | 0 |
| | ½ | — | 50 | 20 | 20 | 0 | 40 | 100 | 10 | 0 | 20 |
| 7 | 2 | — | 100 | 80 | 50 | 60 | 100 | 100 | 10 | 0 | 0 |
| | 1 | — | 100 | 70 | 20 | 0 | 100 | 100 | 10 | 0 | 0 |
| | ½ | — | 90 | 60 | 10 | 10 | 100 | 100 | 20 | 0 | 0 |
| | ¼ | — | 0 | 0 | 0 | 0 | 10 | 90 | 0 | 0 | 0 |
| 8 | 2 | — | 100 | 60 | 0 | 10 | 80 | 100 | 20 | 0 | 0 |
| | 1 | — | 40 | 20 | 0 | 0 | 40 | 90 | 10 | 0 | 0 |
| | ½ | — | 10 | 10 | 0 | 0 | 30 | 90 | 10 | 0 | 0 |
| | ¼ | — | 0 | 0 | 0 | 0 | 10 | 50 | 0 | 0 | 0 |
| 9 | 2 | — | 100 | 90 | 60 | 10 | 100 | 100 | 0 | 0 | 0 |
| | 1 | — | 100 | 90 | 50 | 0 | 100 | 100 | 10 | 0 | 0 |
| | ½ | — | 90 | 10 | 0 | 0 | 90 | 90 | 0 | 0 | 0 |
| | ¼ | — | 90 | 0 | 0 | 0 | 90 | 90 | 0 | 0 | 0 |
| 10 | 2 | — | 90 | 80 | 60 | 10 | 100 | 100 | 0 | 0 | 0 |
| | 1 | — | 70 | 70 | 30 | 0 | 90 | 100 | 0 | 0 | 0 |
| | ½ | — | 10 | 10 | 0 | 0 | 90 | 100 | 0 | 0 | 0 |
| | ¼ | — | 0 | 0 | 0 | 0 | 40 | 90 | 0 | 0 | 0 |

TABLE IV

| Compound No. | Dosage Lbs./Acre | Post-emergence | | | | | | | | | |
|---|---|---|---|---|---|---|---|---|---|---|---|
| | | CG | FM | GF | VL | CB | WM | PW | CT | CN | SB |
| 1 | 2 | — | 90 | 90 | 100 | 100 | 100 | 100 | 90 | 90 | 70 |
| | ½ | — | 90 | 90 | 100 | 90 | 100 | 100 | 100 | 40 | 40 |
| | ¼ | — | 90 | 90 | 90 | 60 | 90 | 90 | 90 | 40 | 50 |
| 2 | 2 | — | 90 | 90 | 100 | 100 | — | — | 90 | 50 | 50 |

TABLE IV-continued

| Compound No. | Dosage Lbs./Acre | Post-emergence | | | | | | | | | |
|---|---|---|---|---|---|---|---|---|---|---|---|
| | | CG | FM | GF | VL | CB | WM | PW | CT | CN | SB |
| | 1 | — | 90 | 90 | 70 | 100 | — | — | 90 | 30 | 40 |
| | ½ | — | 90 | 90 | 60 | 90 | — | — | 90 | 20 | 30 |
| | ¼ | — | 90 | 90 | 40 | 70 | — | — | 70 | 20 | 20 |
| 3 | 2 | — | 90 | 100 | 100 | 100 | 100 | 100 | 90 | 70 | 60 |
| | 1 | — | 90 | 90 | 90 | 100 | 100 | 100 | 90 | 70 | 50 |
| | ½ | — | 70 | 80 | 90 | 90 | 100 | 100 | 90 | 60 | 50 |
| | ¼ | — | 60 | 70 | 80 | 90 | 100 | 100 | 80 | 50 | 40 |
| 4 | 2 | — | 100 | 100 | 100 | 100 | 100 | 100 | 100 | 90 | 60 |
| | ½ | — | 90 | 90 | 100 | 100 | 100 | 100 | 100 | 90 | 30 |
| | ¼ | — | 90 | 80 | 100 | 100 | 100 | 100 | 100 | 80 | 60 |
| 5 | 2 | — | 100 | 90 | 90 | 100 | 100 | 100 | — | 50 | 60 |
| | 1 | — | 100 | 80 | 90 | 70 | 100 | 90 | — | 40 | 50 |
| | ½ | — | 90 | 80 | 70 | 70 | 100 | 90 | — | 20 | 30 |
| | ¼ | — | 60 | 70 | 60 | 60 | 100 | 90 | — | 20 | 20 |
| 6 | 2 | — | 90 | 90 | 100 | 90 | 100 | 100 | 100 | 80 | 70 |
| | 1 | — | 90 | 90 | 100 | 80 | 100 | 100 | 100 | 60 | 80 |
| | ½ | — | 70 | 70 | 100 | 70 | 100 | 100 | 100 | 70 | 80 |
| | ¼ | — | 20 | 40 | 100 | 70 | 100 | 100 | 90 | 30 | 40 |
| 7 | 2 | — | 100 | 100 | 100 | 90 | 100 | 100 | 100 | 90 | 70 |
| | 1 | — | 100 | 90 | 100 | 90 | 100 | 100 | 100 | 80 | 70 |
| | ½ | — | 100 | 90 | 100 | 90 | 100 | 100 | 100 | 80 | 50 |
| | ¼ | — | 50 | 70 | 100 | 80 | 100 | 100 | 100 | 60 | 50 |
| 8 | 2 | — | 90 | 90 | 100 | 90 | — | 100 | — | 90 | 90 |
| | 1 | — | 90 | 90 | 100 | 90 | — | 100 | — | 90 | 90 |
| | ½ | — | 90 | 90 | 100 | 90 | — | 100 | — | 80 | 80 |
| | ¼ | — | 90 | 90 | 100 | 50 | — | 100 | — | 40 | 80 |
| 9 | 2 | — | 100 | 100 | 100 | 90 | — | 100 | — | 70 | 90 |
| | 1 | — | 90 | 90 | 90 | 90 | — | 100 | — | 60 | 90 |
| | ½ | — | 90 | 90 | 90 | 40 | — | 100 | — | 40 | 90 |
| | ¼ | — | 70 | 80 | 90 | 20 | — | 90 | — | 20 | 70 |
| 10 | 2 | — | 100 | 90 | 100 | 100 | 100 | 100 | 100 | 90 | 90 |
| | 1 | — | 90 | 90 | 100 | 100 | 100 | 100 | 100 | 80 | 70 |
| | ½ | — | 90 | 90 | 100 | 100 | 100 | 100 | 100 | 70 | 60 |
| | ¼ | — | 90 | 90 | 90 | 100 | 100 | 100 | 90 | 70 | 60 |

Compounds 2 and 4 were also tested for post-emergence activity under field conditions along with sodium 5-[2-chloro-4-(trifluoromethyl)phenoxy]-2-nitrobenzoate (Compound A). These field tests were conducted as follows:

Field test plots (14′w×60′L) were seeded lengthwise with the following:

Crops: Soybean, cotton, wheat, barley and rice

Weeds: green foxtail, barnyard grass, annual morning glory, velvetleaf, pigweed, wild mustard, and cocklebur.

Treatments were applied 5 weeks after planting with a log sprayer beginning at 1.0 lb A.I.; observations were made at 1.0, 0.5, 0.25 and 0.125 lb rates. Weed control was observed at 13 and 28 days after treatment, using a rating scale of 0 to 100.

Compounds 2 and 4 were formulated as a 2 lb/gal emulsifiable concentrate in mixed xylenes containing 7.3 wt % of Sponto 234 emulsifier. Compound A was formulated as a 2 lb/gal aqueous solution without any adjuvants.

The results of these field tests are set forth in Table V. In this Table BG stands for barnyard grass and MG stands for morning glory.

| Compound No. | Lbs./Acre | % Grass Control At 13 Days | | % Grass Control At 28 Days | | % Broadleaf Control At 13 Days | | | | | % Broadleaf Control At 8 Days | | | | | % Crop Injury At 5 Days |
|---|---|---|---|---|---|---|---|---|---|---|---|---|---|---|---|---|
| | | GF | BG | GF | BG | MG | VL | PW | WM | CB | MG | VL | PW | WM | CB | SB |
| 2 | 1 | 67.5 | 31.5 | 62.0 | 33.8 | 97.5 | 99.5 | 100 | 100 | 99.5 | 100 | 97 | 100 | 100 | 100 | 45.0 |
| | ½ | 20 | 8.8 | 41.2 | 15.0 | 92.5 | 92.5 | 99.5 | 100 | 88.2 | 91.7 | 87.5 | 98.8 | 100 | 83.2 | 38.8 |
| | ¼ | 5.0 | 3.8 | 26.2 | 6.7 | 67.5 | 45.0 | 97.0 | 98.8 | 77.5 | 60.5 | 41.2 | 93.8 | 87.5 | 73.2 | 27.5 |
| | ⅛ | 3.8 | 5.0 | 5.0 | 0 | 52.5 | 35.0 | 88.8 | 95.0 | 69.2 | 18.3 | 16.8 | 90.0 | 75.0 | 49.5 | 25.0 |
| 4 | 1 | 27 | 13.8 | 31.2 | 15.0 | 96.5 | 100 | 100 | 100 | 85.0 | 95.0 | 98.8 | 100 | 100 | 94.5 | 26.5 |
| | ½ | 17.5 | 3.8 | 18.8 | 0 | 78.7 | 100 | 92.8 | 938 | 66.7 | 85.0 | 96.7 | 99.5 | 92.5 | 76.7 | 17.0 |
| | ¼ | 7.5 | 1.3 | 17.5 | 0 | 91.7 | 77.3 | 88.8 | 86.3 | 41.7 | 76.5 | 63.0 | 90.0 | 66.2 | 34.7 | 8.2 |
| | ⅛ | 5.0 | 0 | 12.5 | 0 | 36.7 | 57.3 | 70.0 | 73.8 | 41.7 | 55.0 | 47.0 | 61.2 | 26.2 | 23.8 | 4.5 |
| A | 1 | 91.5 | 42.5 | 94.2 | 42.5 | 96.5 | 100 | 100 | 100 | 98.0 | 91.0 | 81.2 | 100 | 100 | 97.5 | 42.5 |
| | ½ | 52.5 | 22.5 | 78.8 | 16.2 | 95.2 | 91.2 | 97.8 | 100 | 92.5 | 87.7 | 72.5 | 93.8 | 100 | 76.5 | 33.8 |
| | ¼ | 30.0 | 12.5 | 45.0 | 8.8 | 75.0 | 63.8 | 92.8 | 99.0 | 72.0 | 56.0 | 48.0 | 87.0 | 100 | 57.5 | 27.2 |
| | ⅛ | 6.3 | 8.8 | 20.0 | 2.5 | 66.8 | 52.5 | 86.3 | 91.3 | 54.5 | 30.3 | 46.2 | 80.0 | 52.5 | 30.0 | 12.5 |

What is claimed is:

1. A herbicidal compound of the formula

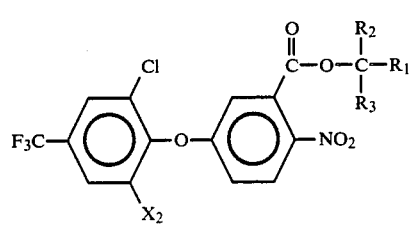

wherein $X_2$ is selected from halogen and hydrogen;
$R_1$ and $R_2$ may be the same or different and each is selected from $QCOOR_6$ and

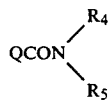

where
Q is $alkyl_{0-3}$;
$R_3$, $R_4$ and $R_5$ are selected from hydrogen and $alkyl_{1-5}$; and
$R_6$ is $alkyl_{1-5}$, hydrogen or cation selected from alkali metals, alkaline earth metals, ammonium, $alkyl_{1-5}$ and $dialkyl_{2-6}$ ammonium.

2. The compound of claim 1 wherein $R_1$ and $R_2$ are $QCOOR_6$.

3. The compound of claim 2 wherein $R_6$ is hydrogen.

4. The compound of claim 1 wherein $R_1$ is $QCOOR_6$, is selected from hydrogen and $alkyl_{1-5}$.

5. The compound of claim 4 wherein $R_2$ is $QCOOR_6$ and $R_6$ is selected from hydrogen and $alkyl_{1-5}$.

6. The compound of claim 5 wherein $R_6$ is said cation.

7. The compound of claim 4 wherein $R_2$ is

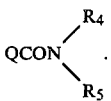

8. The compound of claim 1 wherein $R_1$ is

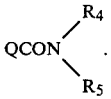

9. The compound of claim 8 wherein $R_2$ is $QCOOR_6$ and $R_6$ is said cation.

10. The compound of claim 1 wherein $R_1$ and $R_2$ are both

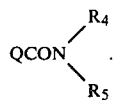

11. The compound of claim 2 wherein $R_6$ is said cation.

12. The compound of claim 1 wherein $R_1$ is $COOC_2H_5$, $R_2$ is $CH_2COOC_2H_5$ or $COOC_2H_5$, and $R_3$ and $X_2$ are hydrogen.

13. A herbicidal composition comprising a herbicidally effective amount of a compound of claim 1 and a carrier therefor.

14. A herbicidal composition comprising a herbicidally effective amount of a compound of claim 12 and a carrier therefor.

15. A method for controlling weeds in a field for crop cultivation which comprises applying to said field prior to emergence of said weeds a herbicidally effective amount of a compound as defined in claim 1, said crop being selected from cotton, corn and soybeans.

16. A method of controlling weeds in a field for crop cultivation which comprises applying to said field prior to emergence of said weeds a herbicidally effective amount of a compound as defined in claim 12, said crop being selected from cotton, corn and soybeans.

17. A method according to claim 16 wherein said crop is cotton.

18. A method according to claim 16 wherein said crop is corn.

19. A method according to claim 16 wherein said crop is soybeans.

20. A method according to claim 15 wherein said compound is applied at a rate of from about ¼ lb/acre to about 2 lbs/acre.

21. A method according to claim 16 wherein said compound is applied at a rate from about ¼ lb/acre to about 2 lbs/acre.

* * * * *